(12) United States Patent
Garcia Molina et al.

(10) Patent No.: US 11,052,220 B2
(45) Date of Patent: Jul. 6, 2021

(54) SYSTEM AND METHOD FOR ADJUSTING THE VOLUME OF AUDITORY STIMULATION DURING SLEEP BASED ON SLEEP DEPTH LATENCIES

(71) Applicants: KONINKLIJKE PHILIPS N.V., Eindhoven (NL); Wisconsin Alumni Research Foundation, Madison, WI (US)

(72) Inventors: Gary Nelson Garcia Molina, Madison, WI (US); Michele Bellesi, Madison, WI (US); Brady Alexander Riedner, Middleton, WI (US); Giulio Tononi, Verona, WI (US)

(73) Assignees: KONINKLIJKE PHILIPS N.V., Eindhoven (NL); Wisconsin Alumni Research Foundation, Madison, WI (US)

( * ) Notice: Subject to any disclaimer, the term of this patent is extended or adjusted under 35 U.S.C. 154(b) by 376 days.

(21) Appl. No.: 16/307,514

(22) PCT Filed: Jun. 26, 2017

(86) PCT No.: PCT/EP2017/065654
§ 371 (c)(1),
(2) Date: Dec. 6, 2018

(87) PCT Pub. No.: WO2018/001936
PCT Pub. Date: Jan. 4, 2018

(65) Prior Publication Data
US 2019/0298967 A1 Oct. 3, 2019

Related U.S. Application Data
(60) Provisional application No. 62/354,902, filed on Jun. 27, 2016.

(51) Int. Cl.
*A61M 21/02* (2006.01)
*A61M 21/00* (2006.01)

(52) U.S. Cl.
CPC ............ *A61M 21/02* (2013.01); *A61M 21/00* (2013.01); *A61M 2021/0016* (2013.01);
(Continued)

(58) Field of Classification Search
CPC .. A61M 21/02; A61M 21/00; A61M 2205/18; A61M 2021/0044;
(Continued)

(56) References Cited

U.S. PATENT DOCUMENTS

2011/0319721 A1* 12/2011 Hamaguchi .......... A61B 5/4812
600/300
2014/0057232 A1 2/2014 Anderson
(Continued)

FOREIGN PATENT DOCUMENTS

WO 2014200433 A1 12/2014
WO 2015049613 A1 4/2015
(Continued)

OTHER PUBLICATIONS

G. Tononi and C. Cirelli, "Sleep function and synaptic homeostasis.," Sleep Med. Rev., vol. 10, No. 1, pp. 49-62, Feb. 2006.
(Continued)

*Primary Examiner* — Kaylee R Wilson (57) ABSTRACT

The present disclosure pertains to a system configured to adjust a volume of auditory stimulation delivered to a subject during sleep. The system is configured to determine a deepening time indicative of a rate at which sleep of the subject deepens during the sleep session. The deepening time is determined based on (i) a ratio of power in a high frequency band of an EEG signal to power in a low frequency band, (ii) a density of slow waves, or (iii) a
(Continued)

hypnogram, indicative of sleep depth in the subject during the sleep session. The system is configured to determine a rate of volume increase for auditory stimulation during a subsequent sleep session based on the deepening time; and control the one or more sensory stimulators to adjust the volume of auditory stimulation provided to the subject during the subsequent sleep session based on the determined rate of volume increase.

21 Claims, 9 Drawing Sheets

(52) U.S. Cl.
CPC ............... *A61M 2021/0022* (2013.01); *A61M 2021/0027* (2013.01); *A61M 2021/0044* (2013.01); *A61M 2021/0083* (2013.01); *A61M 2205/18* (2013.01); *A61M 2205/502* (2013.01); *A61M 2230/10* (2013.01)

(58) Field of Classification Search
CPC .. A61M 2021/0022; A61M 2021/0016; A61M 2021/0027; A61M 2021/0083; A61M 2205/502; A61M 2230/10
See application file for complete search history.

(56) References Cited

U.S. PATENT DOCUMENTS

| 2014/0320309 A1 | 10/2014 | Zhang |
| 2015/0343168 A1 | 12/2015 | Garcia Molina |

FOREIGN PATENT DOCUMENTS

| WO | 2015087188 A1 | 6/2015 |
| WO | 2015092606 A1 | 6/2015 |
| WO | 2016028635 A1 | 2/2016 |

OTHER PUBLICATIONS

B. A. Riedner, B. K. Hulse, F. Ferrarelli, S. Sarasso, and G. Tononi, "Enhancing sleep slow waves with natural stimuli," Medicamundi, vol. 45, No. 2, pp. 82-88, 2010.
International Search Report and Written Opinion, International Application No. PCT/EP2017/065654, dated Oct. 19, 2017.

* cited by examiner

SYSTEM AND METHOD FOR ADJUSTING THE VOLUME OF AUDITORY STIMULATION DURING SLEEP BASED ON SLEEP DEPTH LATENCIES

CROSS-REFERENCE TO PRIOR APPLICATIONS

This application is the U.S. National Phase application under 35 U.S.C. § 371 of International Application Serial No. PCT/EP2017/065654, filed on 26 Jun. 2017, which claims the benefit of U.S. Application Ser. No. 62/354,902, filed on 27 Jun. 2016. These applications are hereby incorporated by reference herein.

BACKGROUND

1. Field

The present disclosure pertains to a system configured to adjust a volume of auditory stimulation delivered to a subject during sleep.

2. Description of the Related Art

Systems for monitoring sleep are known. Sensory stimulation during sleep is known. Sensory stimulation during sleep is often applied continuously and/or at intervals and intensities that do not correspond to sleeping patterns of a subject. The present disclosure overcomes deficiencies in prior art systems.

SUMMARY

Accordingly, one or more aspects of the present disclosure relate to a system configured to adjust a volume of auditory stimulation delivered to a subject during sleep. The system comprises one or more sensory stimulators, one or more sensors, one or more hardware processors, and/or other components. The one or more sensory stimulators are configured to provide the auditory stimulation to the subject. The one or more sensors are configured to generate output signals conveying information related to brain activity in the subject. The one or more hardware processors operatively communicate with the one or more sensory stimulators and the one or more sensors. The one or more hardware processors are configured by machine-readable instructions to: determine brain activity parameters in the subject for a first sleep session based on the output signals, the brain activity parameters including a deepening time indicative of a rate at which sleep of the subject deepens during the first sleep session, wherein the deepening time is determined based on (i) a ratio of power in a high frequency band of an electroencephalogram (EEG) signal to power in a low frequency band, (ii) a density of slow waves in the subject, or (iii) a hypnogram for the first sleep session, indicative of sleep depth in the subject during the first sleep session; determine a rate of volume increase for auditory stimulation provided to the subject during a subsequent sleep session based on the deepening time; and control the one or more sensory stimulators to adjust the volume of auditory stimulation provided to the subject during the subsequent sleep session based on the determined rate of volume increase and the output signals during the subsequent sleep session.

Yet another aspect of the present disclosure relates to a method for adjusting a volume of auditory stimulation delivered to a subject during sleep with an adjustment system. The system comprises one or more sensory stimulators, one or more sensors, one or more hardware processors, and/or other components. The method comprises: providing, with the one or more sensory stimulators, the auditory stimulation to the subject; generating, with the one or more sensors, output signals conveying information related to brain activity in the subject; determining, with the one or more processors, brain activity parameters in the subject for a first sleep session based on the output signals, the brain activity parameters including a deepening time indicative of a rate at which sleep of the subject deepens during the first sleep session, wherein the deepening time is determined based on (i) a ratio of power in a high frequency band of an electroencephalogram (EEG) signal to power in a low frequency band, (ii) a density of slow waves in the subject, or (iii) a hypnogram for the first sleep session, indicative of sleep depth in the subject during the first sleep session; determining, with the one or more processors, a rate of volume increase for auditory stimulation provided to the subject during a subsequent sleep session based on the deepening time; and controlling, with the one or more processors, the one or more sensory stimulators to adjust the volume of auditory stimulation provided to the subject during the subsequent sleep session based on the determined rate of volume increase and the output signals during the subsequent sleep session.

Still another aspect of present disclosure relates to a system for adjusting a volume of auditory stimulation delivered to a subject during sleep. The system comprises: means for providing the auditory stimulation to the subject; means for generating output signals conveying information related to brain activity in the subject; means for determining brain activity parameters in the subject for a first sleep session based on the output signals, the brain activity parameters including a deepening time indicative of a rate at which sleep of the subject deepens during the first sleep session, wherein the deepening time is determined based on (i) a ratio of power in a high frequency band of an electroencephalogram (EEG) signal to power in a low frequency band, (ii) a density of slow waves in the subject, or (iii) a hypnogram for the first sleep session, indicative of sleep depth in the subject during the first sleep session; means for determining a rate of volume increase for auditory stimulation provided to the subject during a subsequent sleep session based on the deepening time; and means for controlling the means for providing auditory stimulation to adjust the volume of auditory stimulation provided to the subject during the subsequent sleep session based on the determined rate of volume increase and the output signals during the subsequent sleep session.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
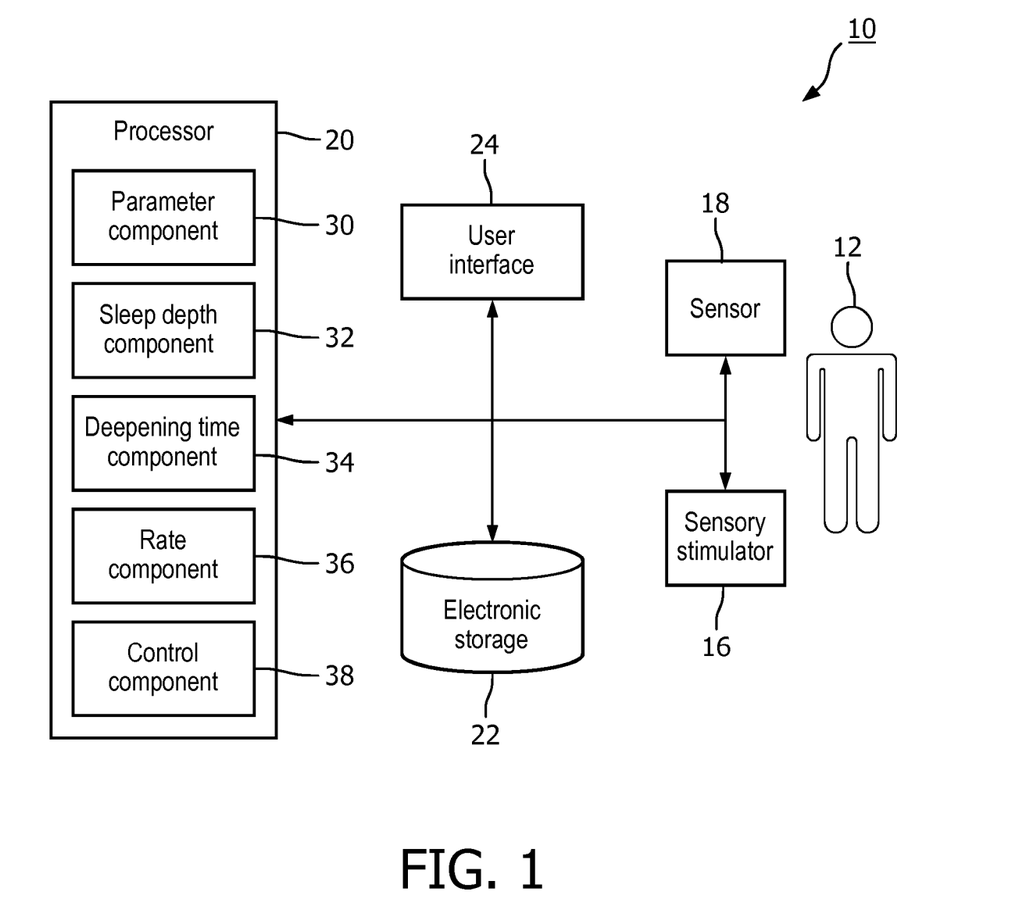
FIG. 1 illustrates a system configured to adjust a volume of auditory stimulation delivered to a subject during sleep.

FIG. 1 is a schematic illustration of a system 10 configured to adjust a volume of auditory stimulation delivered to a subject 12 during sleep. The restorative value of sleep may be enhanced by increasing slow wave activity (SWA) in subject 12 using auditory stimulation during sleep. Within a volume range below a sleep-arousing threshold volume, higher volumes of auditory stimulation produce higher levels of SWA in subject 12. From a subjectively chosen lower volume, the volume of the stimulation may be gradually increased in order to prevent micro-arousals. System 10 is configured such that the dynamics of the volume increase (described below) are adapted to the sleep depth of subject 12 to prevent an excessively fast volume increase that arouses subject 12, and/or to avoid a slow increase in the stimulation volume that can either be inefficacious and/or result in the loudest stimulation being applied during shallow sleep.

Figure 2:
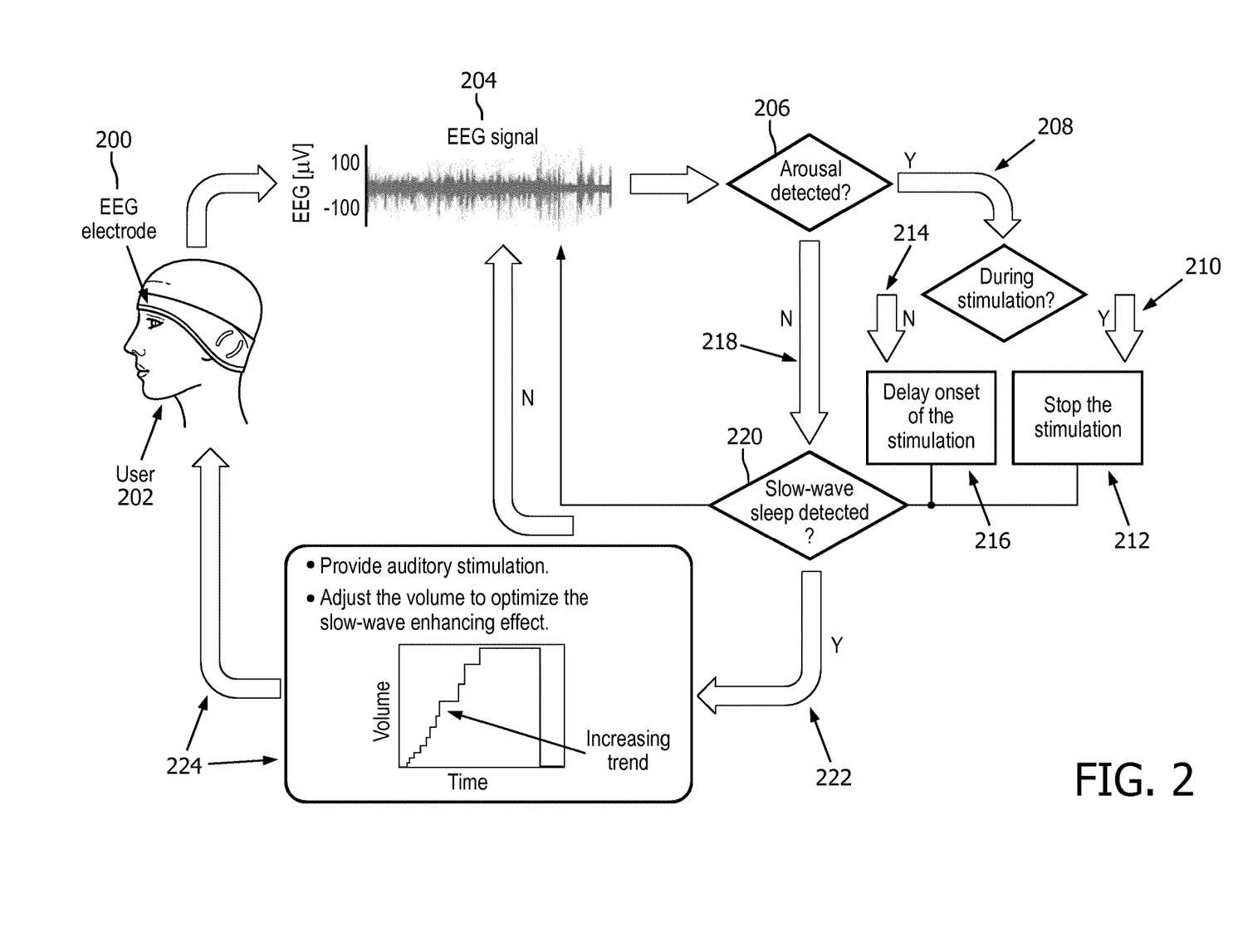
FIG. 2 illustrates typical monitoring of a user's EEG during sleep and delivering auditory stimulation to enhance sleep slow waves without causing arousals.

As described above, auditory stimulation during sleep enhances sleep slow waves and increases the restorative value of sleep. Monitoring a user's electroencephalogram (EEG) during sleep and delivering auditory stimulation to enhance sleep slow waves without causing arousals is known. This process is illustrated in FIG. 2. FIG. 2 illustrates an EEG electrode 200 coupled with a user 202. EEG electrode 200 outputs an EEG signal 204. Typical systems determine 206 the presence of sleep arousal events. Arousal events are detected using thresholds on the EEG power in the higher alpha (8-12 Hz) and beta (15-30) bands. If an arousal is detected 208 during stimulation 210, the stimulation stops immediately 212. If an arousal is detected 208 outside the stimulation period 214, the onset of the next stimulation segment is delayed 216. If no arousal is detected 218, then a typical system proceeds to detect 220, in real-time, the presence of slow wave sleep (e.g., N3 sleep), which is characterized by high activity in the lower delta frequency range (0.5 to 4 Hz) of the EEG. If slow wave sleep is detected for a sufficiently long period of time 222, then a typical system delivers auditory stimulation 224 which consists of a sequence of 50-millisecond long tones separated from each other by a constant 1-second long inter-tone interval. The volume of the auditory stimulation is progressively increased to enhance slow waves in the user. If at time "t" seconds, the SWA (e.g., power in the 0.5 to 4 Hz frequency band of the EEG) in the time window [t−15; t] is lower than the SWA in the time window [t−30; t−15], then the volume of the stimulation is increased by a fixed rate "$r_{fixed}$" proportional to the current volume. If the SWA in the time window [t−15; t] is larger than or equal to the SWA in the time window [t−30; t−15], then the volume remains unchanged.

Figure 3:
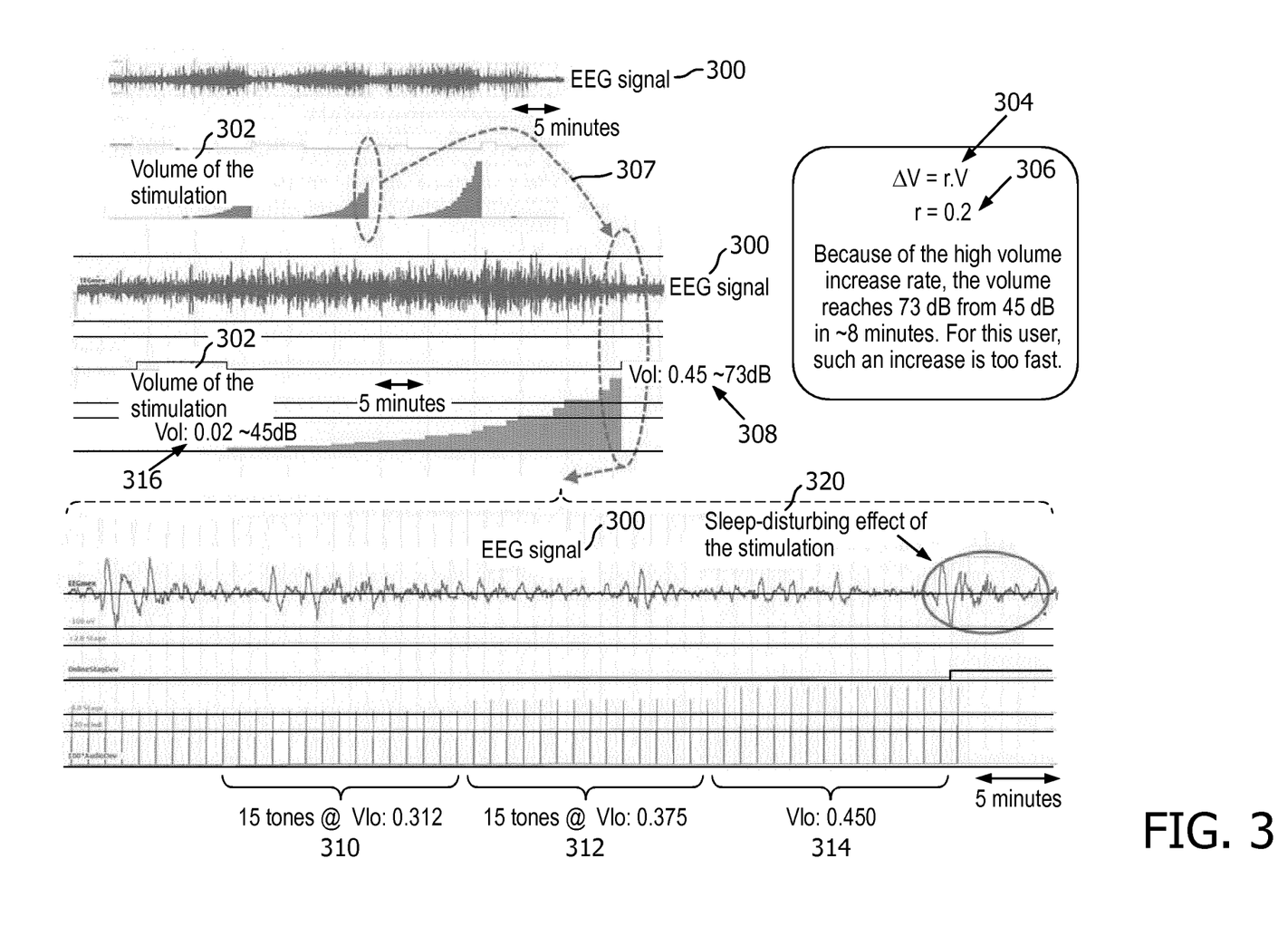
FIG. 3 illustrates an auditory stimulation volume increase rate that risks causing arousals.

If the volume increase rate is too high, then there is a risk of causing arousals in the user. This is illustrated in FIG. 3 where the EEG signals 300 and the stimulation volume 302 are shown for an EEG recording where a volume increase rate 304 was pre-set 306 to 20%. In this example, the volume increase ΔV is related to the current volume as: ΔV=+0.2·V. In this example, the volume reaches 310, 312, 314 a normalized volume of 0.45 (~80+20·log(0.45)=73 dB) 307, 308 starting 316 from 0.02 (~80+20·log(0.02)) in 8 minutes. For the user in the example shown in FIG. 3, the volume increase rate is excessively high because it interrupts 320 slow wave sleep of the user.

Figure 4:
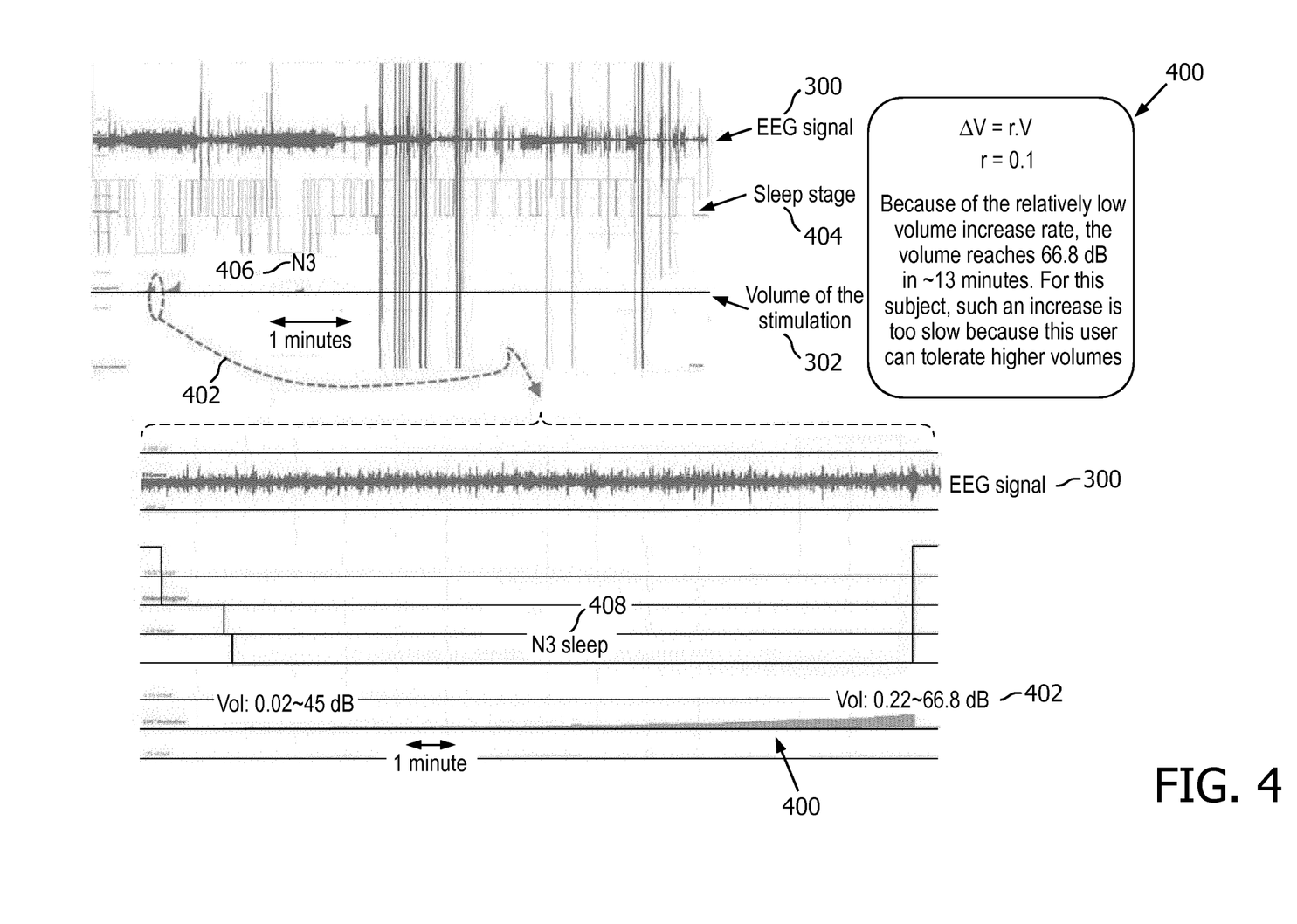
FIG. 4 illustrates an auditory stimulation volume increase rate in a typical system that is too low for a user such that the volume of the stimulation does not reach levels that enhance slow wave activity in the user.

If the volume increase rate is too low for the user, then the volume of the stimulation does not reach levels that enhance SWA in the user. FIG. 4 illustrates a rate 400 of volume increase of 0.1, such that ΔV=+0.1·V, that prevents the stimulation volume from reaching higher levels for a user that can tolerate louder stimulation (e.g., according to experimental perceptual tests performed on the user). For this particular case, the stimulation increases 402 to 66.8 dB starting from 45 dB in about 13 minutes. Another disadvantage of a volume increase rate that is set too low is that the volume may reach louder levels when sleep is in the process of lightening, which can cause arousals. While a relatively long (e.g., a few minutes) period of the signal can be scored (e.g., on a hypnogram) as sleep stage 404 N3 406, the sleep depth within this period is not uniformly low but varies following a U-shaped dynamic where lighter sleep occurs at the beginning and at the end of a continuous (e.g., several minute long) N3 408 sleep period.

Returning to FIG. 1, in some embodiments, system 10 comprises one or more of a sensory stimulator 16, a sensor 18, a processor 20, electronic storage 22, a user interface 24, and/or other components. In FIG. 1, sensory stimulator 16, sensor 18, processor 20, electronic storage 22, and user interface 24 are shown as separate entities. This is not intended to be limiting. Some and/or all of the components of system 10 and/or other components may be grouped into one or more singular devices. For example, some and/or all of the components of system 10 may be grouped as part of a headband and/or other garments worn by subject 12.

Sensory stimulator 16 is configured to provide auditory (e.g., tones) and/or other sensory stimuli to subject 12. Sensory stimulator 16 is configured to provide auditory and/or other sensory stimulation to subject 12 prior to a sleep session, during a sleep session, after a sleep session, and/or at other times. For example, sensory stimulator 16 may be configured to provide auditory stimuli to subject 12 during slow wave sleep in a sleep session. Sensory stimulator 16 may be configured to provide auditory stimulation to subject 12 during a sleep session to induce, maintain, and/or adjust slow wave activity (indicated by EEG power in the 0.5 to 4 Hz band as described below) in subject 12. In some embodiments, sensory stimulator 16 may be configured such that adjusting includes increasing, decreasing, and/or other adjustment of slow wave activity (SWA) in subject 12. In some embodiments, the delivery of the auditory stimulation is timed to correspond to sleep stages associated with SWA, is timed to wake subject 12 from sleep, and/or timed to correspond to other sleep in subject 12.

As described above, sensory stimulator 16 is configured to induce and/or adjust SWA via auditory stimulation of subject 12. In some embodiments, sensory stimulator 16 may be configured to induce and/or adjust SWA through non-invasive brain stimulation and/or other methods. Sensory stimulator 16 may be configured to induce and/or adjust SWA through non-invasive brain stimulation using auditory and/or other sensory stimuli. The other sensory stimuli include odors, visual stimulation, touches, tastes, and/or other stimuli. For example, transcranial magnetic stimulation may be applied to subject 12 to trigger, increase, and/or decrease SWA. Examples of sensory stimulator 16 may include one or more of a music player, a tone generator, one or more speakers, a collection of electrodes on the scalp of subject 12, a unit to deliver vibratory stimulation (also known as somato-sensory stimulation), a coil generating a magnetic field to directly stimulate the brain's cortex, light generators, a fragrance dispenser, and/or other devices.

Sensor 18 is configured to generate output signals conveying information related to brain activity of subject 12 and/or other information. Sensor 18 is configured to generate output signals in an ongoing manner during a sleep session of subject 12, at regular intervals during a sleep session, before a sleep session, after a sleep session, and/or at other times. The brain activity of subject 12 may correspond to sleep depth, a current sleep stage, SWA in subject 12, and/or other characteristics of subject 12. The brain activity of subject 12 may be associated with rapid eye movement (REM) sleep, non-rapid eye movement (NREM) sleep, and/or other sleep. Sleep stages of subject 12 may include one or more of NREM stage N1, stage N2, or stage N3 sleep, REM sleep, and/or other sleep stages. In some embodiments, N1 corresponds to a light sleep state and N3 corresponds to a deep sleep state. In some embodiments, NREM stage 3 or stage 2 sleep may be slow wave (e.g., deep) sleep.

Sensor 18 may comprise one or more sensors that measure such parameters directly. For example, sensor 18 may be and/or include electrodes configured to detect electrical activity along the scalp of subject 12 resulting from current flows within the brain of subject 12. In some embodiments, one or more sensors 18 are EEG electrodes, and/or other sensors. An EEG exhibits changes throughout a sleep session. A prominent change in the EEG delta power (SWA) is typically visible, for example. SWA corresponds to the power of an EEG signal in the 0.5-4.5 Hz band. In some embodiments, this band is set to 0.5-4 Hz. SWA has a typical behavior throughout cyclic variations of a given sleep session. SWA increases during non-rapid eye movement sleep (NREM), declines before the onset of rapid-eye-movement (REM) sleep, and remains low during REM. SWA in successive NREM episodes progressively decreases from one episode to the next. SWA may be estimated, and/or slow wave sleep (e.g., stage N3) may be determined from an EEG for subject 12 during a given sleep session.

Sensor 18 may comprise one or more sensors that generate output signals conveying information related to brain activity of subject 12 indirectly. For example, one or more sensors 18 may generate an output based on a heart rate of subject 12 (e.g., sensor 18 may be a heart rate sensor located on the chest of subject 12, and/or be configured as a bracelet on a wrist of subject 12, and/or be located on another limb of subject 12), movement of subject 12 (e.g., sensor 18 may include a bracelet around the wrist and/or ankle of subject 12 with an accelerometer such that sleep may be analyzed using actigraphy signals), respiration of subject 12, and/or other characteristics of subject 12.

Although sensor 18 is illustrated at a single location near subject 12, this is not intended to be limiting. Sensor 18 may include sensors disposed in a plurality of locations, such as for example, coupled in a removable manner with the skin of subject 12, coupled in a removable manner with clothing of subject 12, worn by subject 12 (e.g., as a headband, wristband, etc.), within (or in communication with) sensory stimulator 16, positioned to point at subject 12 while subject 12 sleeps (e.g., a camera that conveys output signals related to movement of subject 12), and/or in other locations.

Processor 20 is configured to provide information processing capabilities in system 10. As such, processor 20 may comprise one or more of a digital processor, an analog processor, a digital circuit designed to process information, an analog circuit designed to process information, a state machine, and/or other mechanisms for electronically processing information. Processor 20 is configured to operatively communicate with one or more sensory stimulators 16, one or more sensors 18, and/or other components. Although processor 20 is shown in FIG. 1 as a single entity, this is for illustrative purposes only. In some embodiments, processor 20 may comprise a plurality of processing units. These processing units may be physically located within the same device (e.g., sensory stimulator 16, sensor 18), or processor 20 may represent processing functionality of a plurality of devices operating in coordination.

As shown in FIG. 1, processor 20 is configured by machine-readable instructions to execute one or more computer program components. The one or more computer program components comprise one or more of a parameter component 30, a sleep depth component 32, a deepening time component 34, a rate component 36, a control component 38, and/or other components. Processor 20 may be configured to execute components 30, 32, 34, 36, 38 and/or other components by software; hardware; firmware; some combination of software, hardware, and/or firmware; and/or other mechanisms for configuring processing capabilities on processor 20.

It should be appreciated that although components 30, 32, 34, 36, and 38 are illustrated in FIG. 1 as being co-located within a single processing unit, in embodiments in which processor 20 comprises multiple processing units, one or more of components 30, 32, 34, 36, 38, and/or other components may be located remotely from the other components. The description of the functionality provided by the different components 30, 32, 34, 36, 38, and/or other components described below is for illustrative purposes, and is not intended to be limiting, as any of components 30, 32, 34, 36, and/or 38 may provide more or less functionality than is described. For example, one or more of components 30, 32, 34, 36, and/or 38 may be eliminated, and some or all of its functionality may be provided by other components 30, 32, 34, 36, and/or 38. As another example, processor 20 may be configured to execute one or more additional components that may perform some or all of the functionality attributed below to one of components 30, 32, 34, 36, and/or 38.

Parameter component 30 is configured to determine brain activity parameters in subject 12 during a sleep session. Parameter component 30 is configured to determine the brain activity parameters based on the output signals and/or other information. In some embodiments, the one or more brain activity parameters include EEG related parameters such as power in various frequency bands of the EEG, ratios of power in a high (e.g., alpha, beta) frequency band to power in a low (e.g., delta, theta) frequency band, and/or other parameters. In some embodiments, parameter component 30 is configured such that the one or more brain activity parameters are and/or are related to a frequency, amplitude, phase, and/or presence of specific sleep patterns such as spindles, K-complexes, or sleep slow waves, alpha waves, and/or other characteristics of the EEG signal. In some embodiments, determining the one or more brain activity parameters includes additively combining and/or performing other mathematical operations on the individual oscillatory components related to brain activity. For example, in some embodiments, the one or more brain activity parameters are determined based on the frequency, amplitude, and/or other characteristics of the EEG signal. In some embodiments, the determined brain activity parameters and/or the characteristics of the EEG may be and/or indicate sleep states that correspond to REM and/or NREM sleep stages. In some embodiments, the determined brain activity parameters are the REM and/or NREM sleep stages described above.

In some embodiments, the brain activity parameters include one or more of a power in a low frequency band (e.g., about 0 to about 6 Hz) of an EEG signal, a power in a high frequency (e.g., about 8 to about 40 Hz), a ratio of power in a high frequency band of an EEG signal to power in a low frequency band, the log of such a ratio, a density of slow waves in subject 12, a frequency of spindles in subject 12, a peak to peak amplitude of the slow waves in subject 12, and/or other parameters. Parameter component 30 is configured to detect individual slow waves by detecting a negative going zero-crossing followed by a positive going zero-crossing in an EEG signal where the amplitude of the negative peak is below a predetermined threshold (e.g., −40 microvolts and/or any other threshold that allows system 10 to function as described herein) and the time period between the zero crossings is longer than a second predetermined threshold (e.g., 200 milliseconds and/or any other threshold that allows system 10 to function as described herein). In some embodiments, parameter component 30 is configured to determine brain activity parameters in subject 12 in an ongoing manner during the sleep session, at predetermined intervals during the sleep session, and/or at other times.

In some embodiments, the brain activity parameters include sleep depth. Sleep depth component 32 is configured to determine the sleep depth of subject 12 during a (e.g., first) sleep session. In some embodiments, the sleep session may be a calibration and/or other sleep sessions. Determining the sleep depth of subject 12 includes determining (i) a ratio of power in a high frequency band of an EEG signal to power in a low frequency band, (ii) a density of slow waves in subject 12, (iii) a hypnogram for the first sleep session, a frequency of spindles in subject 12, and/or other parameters indicative of sleep depth in subject 12. In some embodiments, the ratio of power in the high frequency band of the EEG signal to power in the low frequency band is and/or includes a log of the power ratio between the alpha (8-12 Hz) or beta (15-30 Hz) bands, and the delta (0.5-4 Hz) or theta (4-8 Hz) bands of the EEG signal. In some embodiments, the density of slow waves in subject 12 may be and/or include a density of detected sleep slow waves in a given time period (e.g., a number of detected slow waves in 20 seconds). In some embodiments, the hypnogram is manually determined (e.g., by a caregiver) and/or automatically determined by sleep depth component 32 and/or other components of processor 20.

In some embodiments, sleep depth component 32 is configured to determine sleep depth based on a ratio (e.g., the beta-delta ratio ($\beta/\delta$) and/or any other high frequency band power to low frequency band power ratio) determined in real-time or near real-time based on a filtered EEG signal (e.g., from sensor 18). In some embodiments, sleep depth component 32 determines a running average (e.g., to ensure the smooth variation of this ratio a 30-second long (this is not intended to be limiting) averaging is used) of squared filtered signals and determines the ratio based on this running average. In some embodiments, sleep depth component 32 is configured such that the sleep depth is the determined value of the ratio.

As described above, in some embodiments, sleep depth component 32 is configured to determine sleep depth based on a density of slow waves in subject 12. Sleep depth component 32 and parameter component 30 are configured such that density of slow waves in subject 12 is the number of slow-waves detected (e.g., by parameter component 30) during N3 sleep in subject 12 during time windows of predetermined lengths (e.g., a 20-second long window and/or a window of any other length that allows system 10 to function as described herein). The time windows of predetermined length may be set at manufacture, determined by sleep depth component 32 based on previous sleep of subject 12, set by a user via user interface 24, and/or determined by other methods. In some embodiments, sleep depth component 32 is configured such that the sleep depth is indicated by the number of slow waves in the predetermined time period.

In some embodiments, the brain activity parameters include a deepening time. A deepening time is indicative of a rate at which sleep of subject 12 deepens during a (e.g., the first) sleep session. Deepening time component 34 is configured to determine the deepening time based on (i) the ratio of power in the high frequency band of the EEG signal to power in the low frequency band, (ii) the density of slow waves in subject 12, (iii) the hypnogram for the first sleep session, and/or other parameters indicative of sleep depth in subject 12 (e.g., as described above) determined by sleep depth component 32. The deepening time (e.g., "T" in the equations below) is the time between two predefined thresholds on the sleep depth. The two predefined thresholds on sleep depth may be set at manufacture of system 10, set by subject 12 and/or other users via user interface 24, determined by deepening time component 34, and/or determined by other methods.

Figure 5:
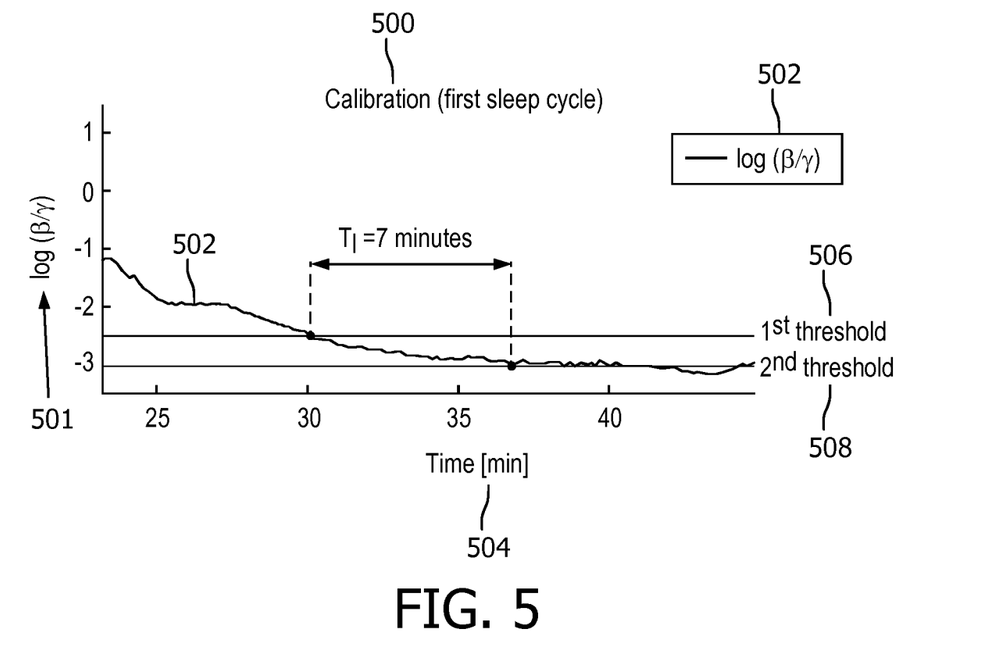
FIG. 5 illustrates sleep depth during a sleep session.

In embodiments where sleep depth component 32 determines sleep depth as the log of the beta to delta ratio (log(β/δ)), deepening time component 34 is configured such that two predefined thresholds (e.g., "−2.5" and "−3" but this is not intended to be limiting) are set on the log(β/δ) curve. The log(β/δ) curve decreases progressively as sleep deepens and the timing at which the curve crosses the thresholds is used to define the deepening time "T". This is illustrated in FIG. 5. FIG. 5 illustrates a (e.g., calibration) sleep session 500. The log(β/δ) 501 curve 502 decreases over time 504. Two predefined thresholds 506, 508 are set to −2.5 and −3 respectively. The time between the log(β/δ) curve breaching threshold 506 and threshold 508 (as shown in FIG. 5, threshold 508 is lower than threshold 506) is the deepening time T (e.g., 7 minutes). In this example deepening time component 34 (FIG. 1) determines the log of the ratio between the power in the beta band (15 to 30 Hz) and the power in the delta band (0.5 to 4 Hz) of the EEG signal. The power in these bands is determined (e.g., by parameter component 30 shown in FIG. 1) using the power spectrum density in 6-second long epochs following the Welch method (e.g., a 4 second long window with 2 second long overlap).

Returning to FIG. 1, in embodiments where sleep depth component 32 determines sleep depth as the density of slow waves in subject 12 in a given period of time, deepening time component 34 is configured to set the predefined thresholds to two different levels of detected slow waves for the given period of time (e.g., 5 and 10 slow-waves/20 seconds). The density of slow-waves increases as sleep deepens and the timing at which the thresholds are crossed are used to define the deepening time T. In embodiments where sleep depth component 32 determines sleep depth as the hypnogram for the (e.g., calibration) sleep session, which provides a discretized version of sleep depth, deepening time component 34 is configured such that the thresholds are defined in terms of the time from which a first N3 epoch is annotated and the time of a first transition from N3 to N2.

Figure 6:
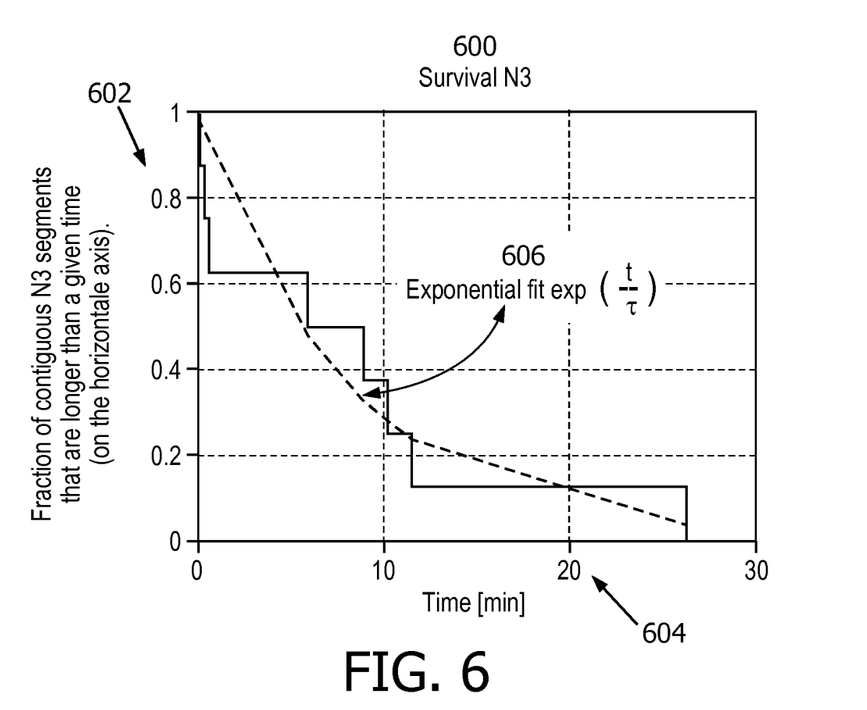
FIG. 6 illustrates estimating survival by fitting an exponential function to a distribution of contiguous N3 segments.

In some embodiments, deepening time component 34 is configured such that the deepening time is determined by fitting an exponential function to a distribution of contiguous N3 sleep segments in the (e.g., first) sleep session of subject 12. In embodiments where sleep depth component 32 determines sleep depth as the hypnogram for the (e.g., calibration) sleep session, deepening time component 34 is configured to determine the N3 survival duration as the average duration of continuous N3 segments. The survival can also be estimated by fitting an exponential function to the distribution of the duration of contiguous N3 segments (or bouts). This is illustrated in FIG. 6. FIG. 6 illustrates N3 survival 600 which provides the probability of a contiguous N3 segment to last longer than a given time. The vertical axis in the plot shown in FIG. 6 is the fraction of contiguous N3 segments 602 that are longer than a given time 604. Given time 604 is shown on the horizontal axis of the plot shown in FIG. 6. The deepening time is determined by fitting 606 an exponentially decreasing function to the distribution of contiguous N3 sleep segments. The deepening time needed for the determination of the rate of volume increase (described below) is then be determined by setting T=r where r is the time constant in the exponentially decreasing function 606.

In some embodiments, deepening time component 34 is configured to determine the deepening time T based on a combination of one or more of the methods described above (e.g., based on a combination of one of more of the time between the predefined thresholds on log(β/δ), slow wave density, and/or the hypnogram; and/or the exponential function fitting). The combination strategy comprises taking the weighted average of deepening times obtained with each method. Since the log(β/δ) curve has a better temporal resolution to determine the deepening time, the deepening time obtained with this method can have a higher weight in the average.

Rate component 36 is configured to determine a rate of volume increase for auditory stimulation provided to subject 12 during a subsequent (e.g. a second) sleep session. Rate component 36 is configured to determine the rate of volume increase based on the deepening time and/or other information. Using the deepening time as determined by sleep depth component 32 and deepening time component 34 in any of the embodiments described above, the rate of volume increase is determined using the model in Eq. (1)

$$\frac{dV}{dt} = rV, \quad (1)$$

where "V" is the volume at time "t", and "r" is the rate of volume increase. This implies that:

$$\Rightarrow \int_{V=V_m}^{V_M} \frac{dV}{V} = \int_{t=0}^{T} r \, dt, \quad (2)$$

$$\Rightarrow \ln\left(\frac{V_M}{V_m}\right) = rT \Rightarrow r = \frac{1}{T}\ln\left(\frac{V_M}{V_m}\right), \quad (3)$$

where "$V_M$" and "$V_m$" are the maximum and minimum volume respectively which are subjectively selected for each user (described below), and "T" is the deepening time which can be determined by any of the methods described above (e.g., based on one or more of the predefined thresholds on log(β/δ), slow wave density, and/or the hypnogram; and/or the exponential function fitting).

In some embodiments, rate component 36 is configured such that the rate of volume increase is determined based on a minimum threshold volume and a maximum threshold volume selected for subject 12. In some embodiments, rate component 36 is configured such that the minimum threshold volume and the maximum threshold volume remain unchanged during a sleep session. The minimum threshold volume and the maximum threshold volume are selected based on information related to brain activity in subject 12 from previous sleep sessions, based on previous sleep depth estimates during the previous sleep sessions; based on corresponding volume thresholds for a demographically similar population, and/or based on other information. In some embodiments, the minimum and maximum threshold volumes are determined based on a maximum and/or minimum frequency and/or volume subject 12 is able to perceive while awake. In some embodiments, rate component 36 is configured such that the volume limits are subjectively set by, for instance, setting the minimum volume to the hearing threshold of subject 12 and the maximum volume to the volume level that can wake up subject 12 (e.g., the volume of a wake up alarm set by subject 12). It is also possible that the volume limits are set by analyzing the sleep EEG data from a calibration night and identifying sensitive subjects.

Control component 38 is configured to control sensory stimulator 16 to provide sensory stimulation to subject 12. Control component 38 is configured to control sensory stimulator 16 to adjust the volume of auditory stimulation provided to subject 12 during the subsequent (e.g., second) sleep session. Control component 38 is configured to control sensory stimulator 16 based on the determined rate of volume increase, the output signals during the subsequent sleep session, and/or other information. In some embodiments, control component 38 is configured such that controlling sensory stimulator 16 to adjust the volume of auditory stimulation provided to subject 12 during the subsequent (e.g., second) sleep session based on the determined rate of volume increase and the output signals during the subsequent sleep session includes: determining sleep depth in subject 12 during the subsequent sleep session based on one or more of the ratio, the density of slow waves, or a peak to peak slow wave amplitude during the subsequent sleep session; and controlling sensory stimulator 16 to adjust the volume of auditory stimulation provided to subject 12 during the subsequent sleep session based on the determined sleep depth during the subsequent sleep session and the determined rate of volume increase.

Figure 7:
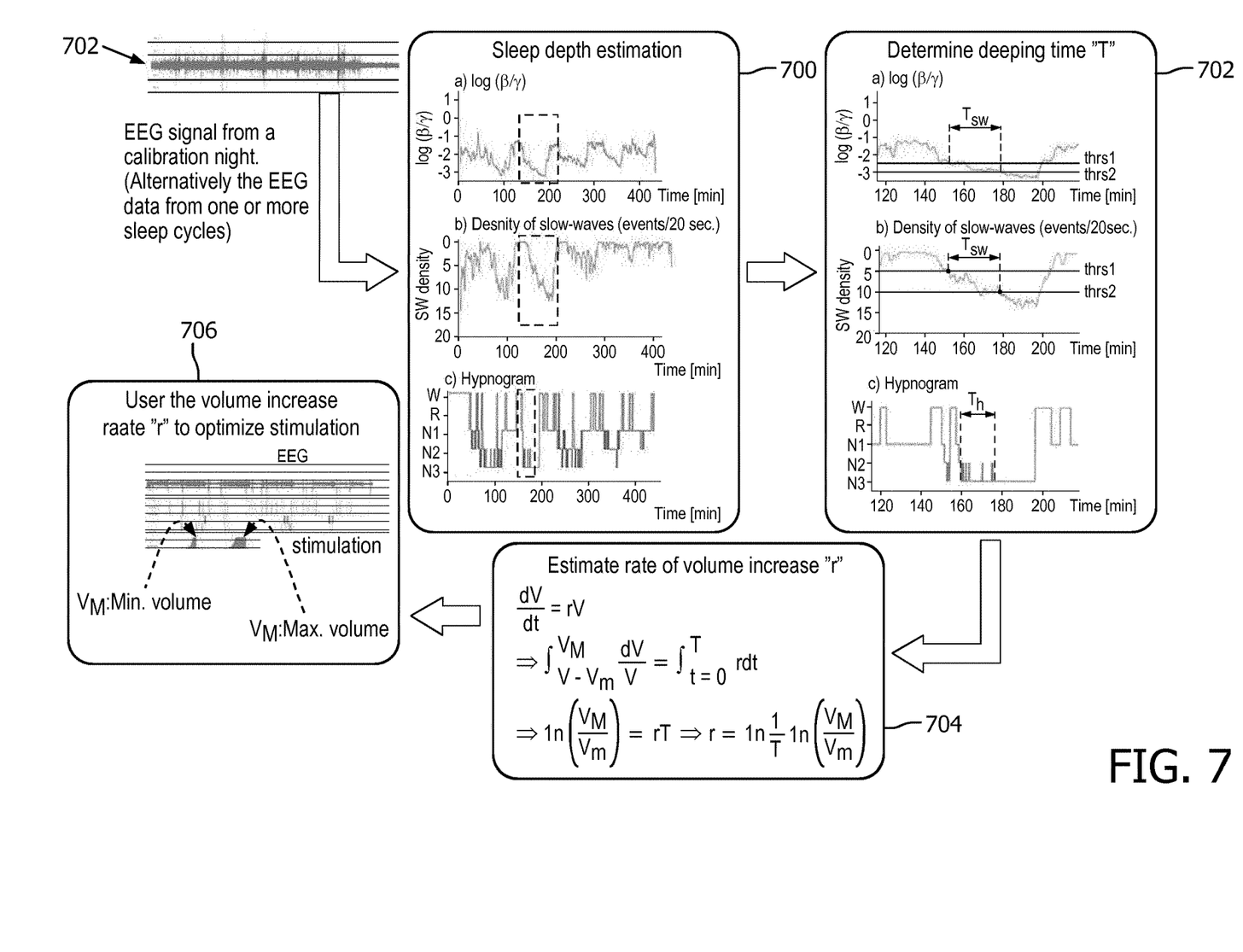
FIG. 7 summarizes the operations performed by the present system.

FIG. 7 summarizes the operations performed by system 10 (shown in FIG. 1). FIG. 7 illustrates sleep depth determination 700 (e.g., by sleep depth component 32) based on EEG signals 702 from a calibration (e.g., first) sleep session. FIG. 7 illustrates determining sleep depth as 700 (*a*) the $\log(\beta/\delta)$ ratio, 700 (*b*) the density of slow waves, and 700 (*c*) the hypnogram. The deepening time "T" is determined 702 (e.g., by deepening time component 34 shown in FIG. 1) based on sleep depth determination 700 and/or other information. As shown in 702 (*a*), the predefined thresholds are set to −2.5 and −3 (these are not intended to be limiting). The $\log(\beta/\delta)$ curve decreases progressively as sleep depends and the timing at which the thresholds are crossed are used to define the deepening time "$T_l$". As shown in 702 (*b*), the predefined thresholds are set to 5 and 10 slow-waves/20 seconds (this is not intended to be limiting). The density of slow waves increases as sleep deepens and the timing at which the thresholds are crossed are used to define the deepening time "$T_{sw}$". As shown in 702 (*c*), hypnogram thresholds are defined in terms of the time from which the first N3 epoch is annotated and the time of the first transition from N3 to N2. These are used to define the deepening time "$T_h$". Using the deepening time as determined by any of the methods described above, the rate of volume increase is determined 704 (e.g., by rate component 36 shown in FIG. 1) using the model in Eq. (1), (2), and/or (3). Finally, control component 38 (FIG. 1) is configured to control one or more sensory stimulators 16 (FIG. 1) to adjust 706 the volume of auditory stimulation provided to subject 12 during a subsequent (e.g., second) sleep session based on the determined rate of volume increase, the output signals during the subsequent sleep session, and/or other information.

Figure 8A:
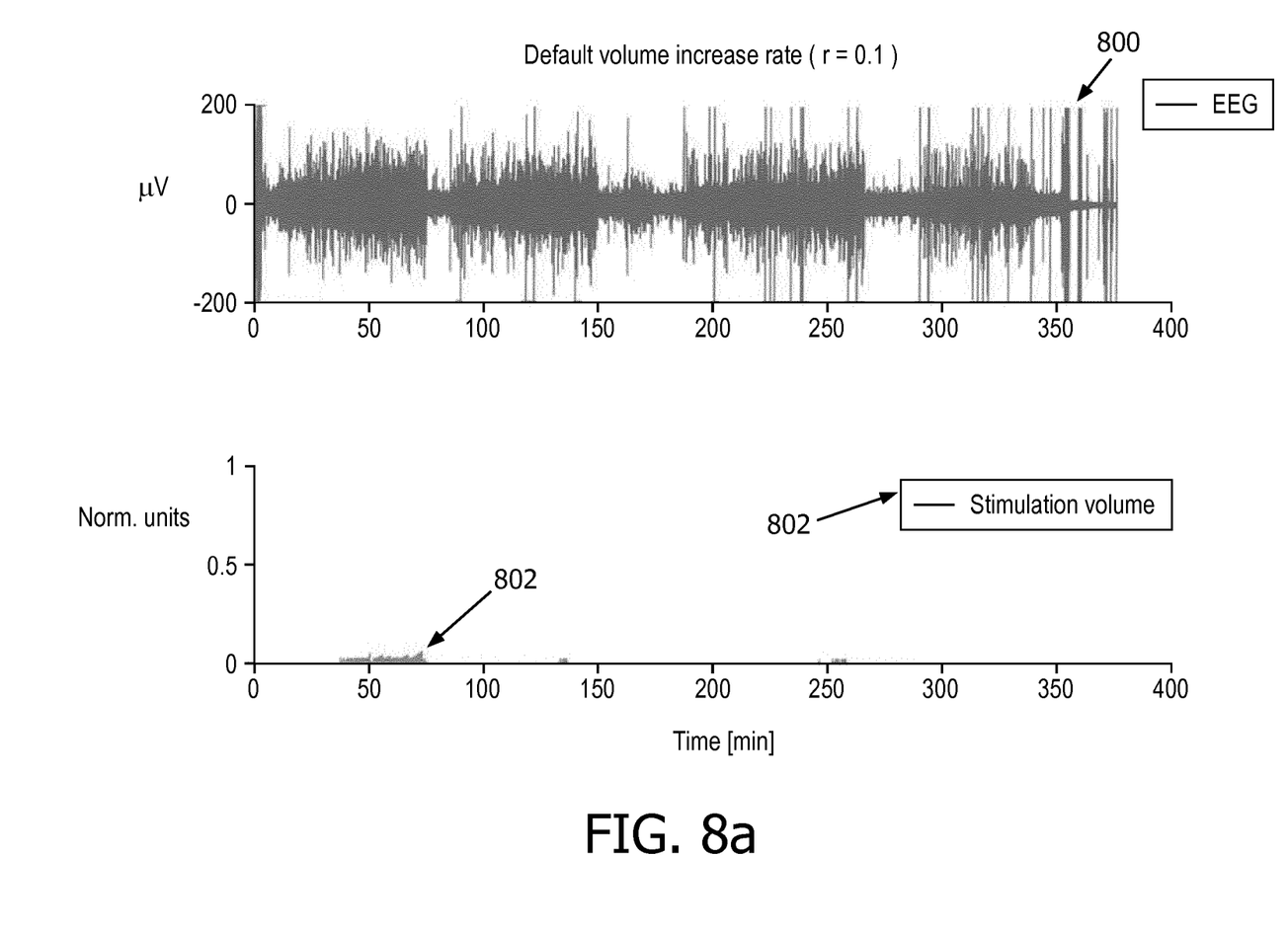
FIG. 8 illustrates experimental results gathered using the present system.
Figure 8B:
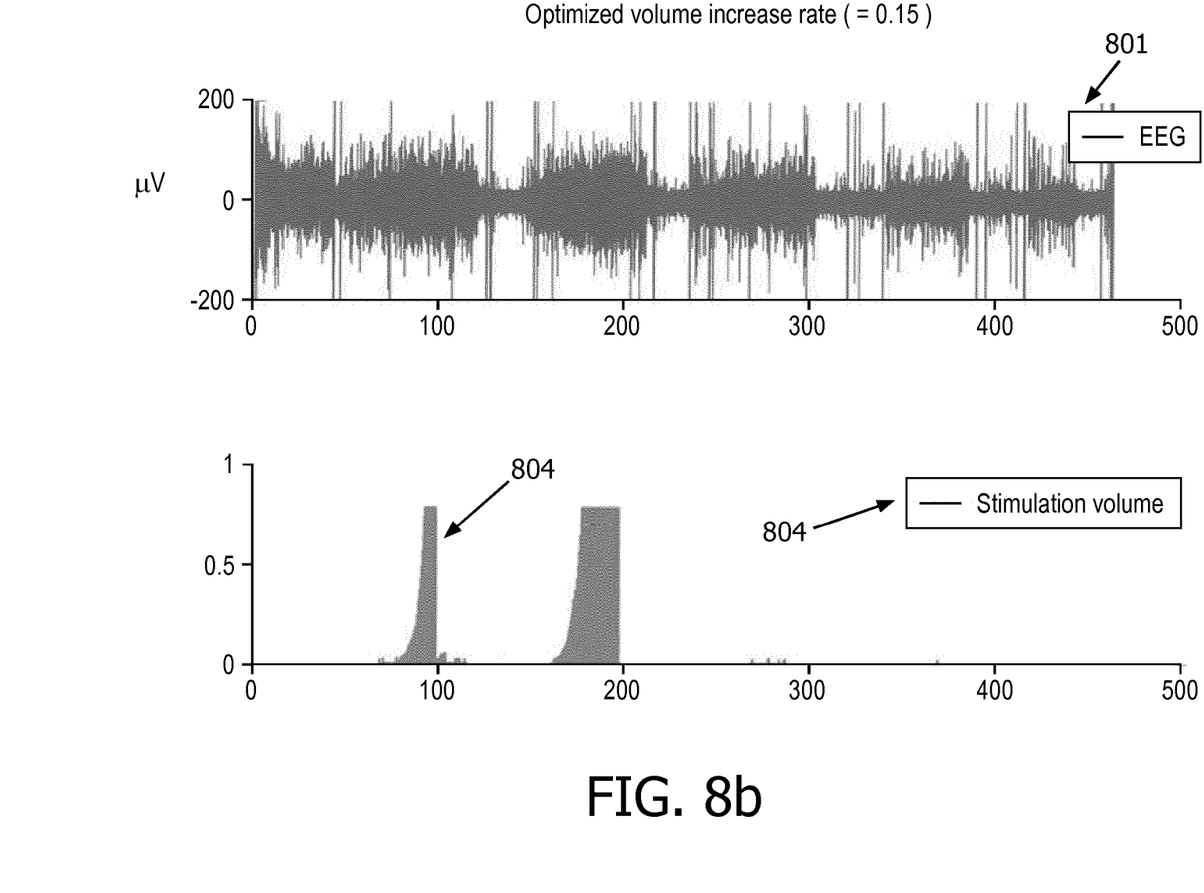

FIG. 8 illustrates experimental results gathered using system 10. To gather the experimental results shown in FIG. 8, EEG signals recorded during a first sleep night of a user (e.g., subject 12) were used to determine (as described above) a deepening time of 7 minutes (e.g., as shown in FIG. 5) for that user. Using the deepening time of 7 minutes, the rate of volume increase "r" is 0.01 units per second. If the increase is made every 15 seconds, the increase rate is 0.15 units every 15 seconds. Two tests were then conducted during subsequent sleep sessions. First, stimulation using a default volume increase rate of 0.1 units every 15 seconds typical for previous systems was provided to the user. This is illustrated in FIG. 8 (*a*). Second, stimulation using the adjusted volume increase rate of 0.15 units every 15 seconds (determined by system 10) was provided to the user. This is illustrated in FIG. 8 (*b*). FIG. 8 (*a*) and FIG. 8 (*b*) illustrate EEG signals 800 and 801 that correspond to volume increase rates of 0.1 and 0.15 respectively. As shown in FIG. 8 (*a*) and FIG. 8 (*b*), the volume of the stimulation 802, 804 reaches higher (more effective at increasing SWA) levels when the adjusted volume increase rate (FIG. 8 (*b*)) is used without arousing the user.

Returning to FIG. 1, electronic storage 22 comprises electronic storage media that electronically stores information. The electronic storage media of electronic storage 22 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 22 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Electronic storage 22 may store software algorithms, information determined by processor 20, information received via user interface 24 and/or external computing systems, and/or other information that enables system 10 to function properly. Electronic storage 22 may be (in whole or in part) a separate component within system 10, or electronic storage 22 may be provided (in whole or in part) integrally with one or more other components of system 10 (e.g., processor 20).

User interface 24 is configured to provide an interface between system 10 and subject 12, and/or other users through which subject 12 and/or other users may provide information to and receive information from system 10. This enables data, cues, results, and/or instructions and any other communicable items, collectively referred to as "information," to be communicated between a user (e.g., subject 12) and one or more of sensory stimulator 16, sensor 18, processor 20, and/or other components of system 10. For example, an EEG may be displayed to a caregiver via user interface 24.

Examples of interface devices suitable for inclusion in user interface 24 comprise a keypad, buttons, switches, a keyboard, knobs, levers, a display screen, a touch screen, speakers, a microphone, an indicator light, an audible alarm, a printer, a tactile feedback device, and/or other interface devices. In some embodiments, user interface 24 comprises a plurality of separate interfaces. In some embodiments, user interface 24 comprises at least one interface that is provided integrally with sensory stimulator 16 and/or other components of system 10.

It is to be understood that other communication techniques, either hard-wired or wireless, are also contemplated by the present disclosure as user interface 24. For example, the present disclosure contemplates that user interface 24 may be integrated with a removable storage interface provided by electronic storage 22. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 24 comprise, but are not limited to, an RS-232 port, RF link, an IR link, modem (telephone, cable or other). In short, any technique for communicating information with system 10 is contemplated by the present disclosure as user interface 24.

Figure 9:
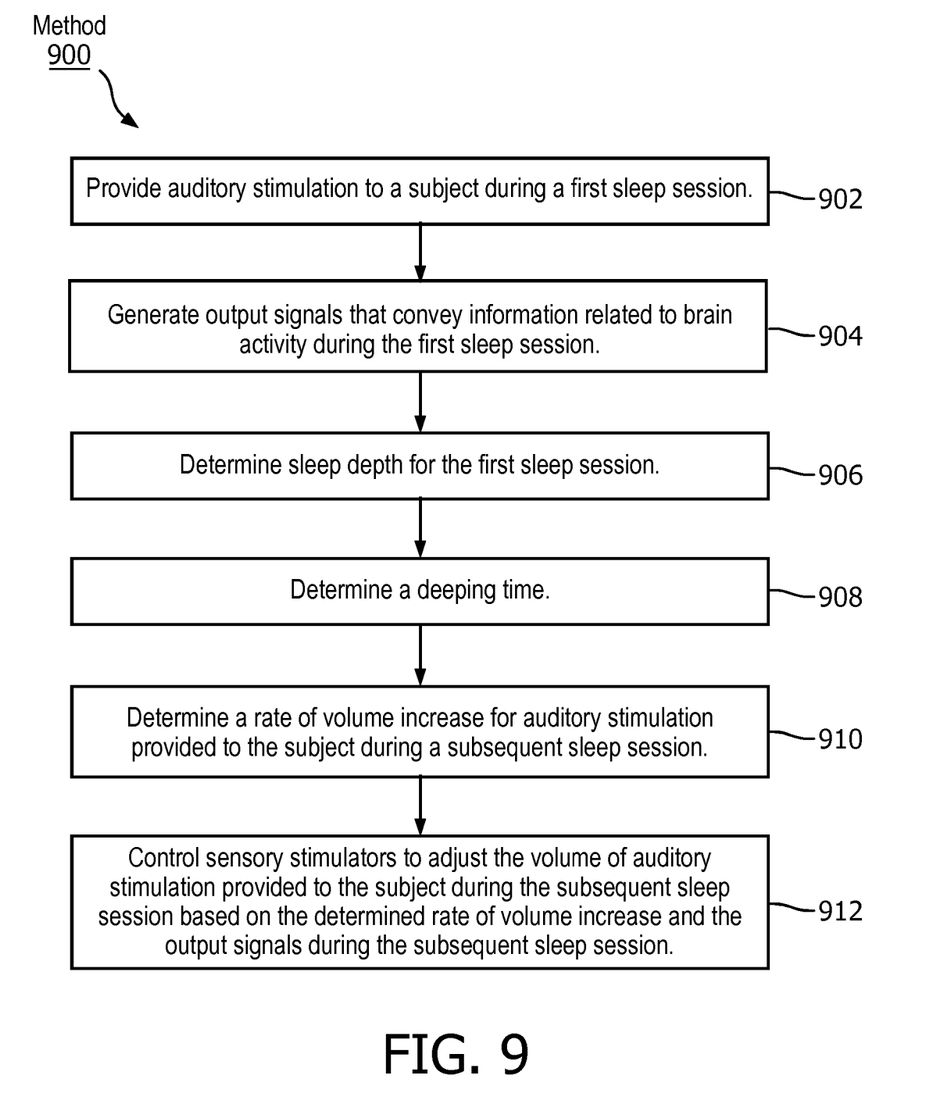
FIG. 9 illustrates a method for adjusting a volume of auditory stimulation delivered to a subject during sleep with an adjustment system.

FIG. 9 illustrates a method 900 for adjusting a volume of auditory stimulation delivered to a subject during sleep with an adjustment system. The system comprises one or more sensory stimulators, one or more sensors, one or more hardware processors, and/or other components. The operations of method 900 presented below are intended to be illustrative. In some embodiments, method 900 may be accomplished with one or more additional operations not described, and/or without one or more of the operations discussed. Additionally, the order in which the operations of method 900 are illustrated in FIG. 9 and described below is not intended to be limiting.

In some embodiments, method 900 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 900 in response to instructions stored electronically on an electronic storage medium. The one or more processing devices may include one or more devices configured through hardware, firmware, and/or software to be specifically designed for execution of one or more of the operations of method 900.

At an operation 902, auditory stimulation is provided to a subject during a first sleep session. In some embodiments, operation 902 is performed by one or more sensory stimulators the same as or similar to sensory stimulators 16 (shown in FIG. 1 and described herein). As described above, in some embodiments, the one or more sensory stimulators comprise a tone generator, a speaker, and/or other components.

At an operation 904, output signals conveying information related to brain activity of the subject during the first sleep session are generated. In some embodiments, operation 904 is performed by one or more sensors the same as or similar to sensors 18 (shown in FIG. 1 and described herein). In some embodiments, as described above, the one or more sensors comprise EEG electrodes and/or other sensors.

At an operation 906, sleep depth for the first sleep session is determined. The sleep depth is and/or is determined based on (i) a ratio of power in a high frequency band of an electroencephalogram (EEG) signal to power in a low frequency band, (ii) a density of slow waves in the subject, (iii) a hypnogram for the first sleep session, and/or other parameters. In some embodiments, determining sleep depth includes determining sleep depth over time for the first sleep session. The sleep depth over time determination is based on (i) the ratio of power in the high frequency band of the EEG signal to power in the low frequency band, (ii) the density of slow waves in the subject, (iii) the hypnogram for the first sleep session, and/or other information. In some embodiments, operation 906 is performed by a hardware processor component the same as or similar to sleep depth component 32 (shown in FIG. 1 and described herein).

At an operation 908, a deepening time is determined. The deepening time is indicative of a rate at which sleep of the subject deepens during the first sleep session. In some embodiments, the deepening time is an amount of time between two predetermined sleep depth thresholds on a sleep depth over time plot. In some embodiments, the deepening time is determined by fitting an exponential function to a distribution of contiguous N3 sleep segments in the first sleep session of the subject. In some embodiments, operation 908 is performed by a hardware processor component the same as or similar to deepening time component 34 (shown in FIG. 1 and described herein).

At an operation 910, a rate of volume increase for auditory stimulation provided to the subject during a subsequent sleep session is determined. The rate of volume increase is determined based on the deepening time and/or other information. In some embodiments, the rate of volume increase is further determined based on a minimum threshold volume and a maximum threshold volume selected for the subject. The minimum threshold volume and the maximum threshold volume are selected based on information related to brain activity in the subject from previous sleep sessions, based on previous sleep depth estimates during the previous sleep sessions, based on corresponding volume thresholds for a demographically similar population, and/or based on other information. In some embodiments, operation 910 is performed by a hardware processor component the same as or similar to rate component 36 (shown in FIG. 1 and described herein).

At an operation 912, the sensory stimulators are controlled to adjust the volume of auditory stimulation provided to the subject during the subsequent sleep session. The volume adjustment is based on the determined rate of volume increase and the output signals during the subsequent sleep session. In some embodiments, controlling the one or more sensory stimulators to adjust the volume of auditory stimulation provided to the subject during the subsequent sleep session based on the determined rate of volume increase and the output signals during the subsequent sleep session includes: determining sleep depth in the subject during the subsequent sleep session based on one or more of the ratio, the density of slow waves, or a peak to peak slow wave amplitude during the subsequent sleep session; and controlling the one or more sensory stimulators to adjust the volume of auditory stimulation provided to the subject during the subsequent sleep session based on the determined sleep depth during the subsequent sleep session and the determined rate of volume increase. In some embodiments, operation 912 is performed by a hardware processor component the same as or similar to control component 38 (shown in FIG. 1 and described herein).

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system configured to adjust a volume of auditory stimulation delivered to a subject during sleep, the system comprising:
   one or more sensory stimulators configured to provide the auditory stimulation to the subject;
   one or more sensors configured to generate output signals conveying information related to brain activity in the subject; and
   one or more hardware processors operatively communicating with the one or more sensory stimulators and the one or more sensors, the one or more hardware processors configured by machine-readable instructions to:
    determine brain activity parameters in the subject for a first sleep session based on the output signals, the brain activity parameters including a deepening time indicative of a rate at which sleep of the subject deepens during the first sleep session, wherein the deepening time is determined based on (i) a ratio of power in a high frequency band of an electroencephalogram (EEG) signal to power in a low frequency band, (ii) a density of slow waves in the subject, or (iii) a hypnogram for the first sleep session, indicative of sleep depth in the subject during the first sleep session;
    determine a rate of volume increase for auditory stimulation provided to the subject during a subsequent sleep session based on the deepening time; and
    control the one or more sensory stimulators to adjust the volume of auditory stimulation provided to the subject during the subsequent sleep session based on the determined rate of volume increase and the output signals during the subsequent sleep session.

2. The system of claim 1, wherein the one or more hardware processors are configured such that the rate of volume increase is further determined based on a minimum threshold volume and a maximum threshold volume selected for the subject, the minimum threshold volume and the maximum threshold volume selected based on information related to brain activity in the subject from previous sleep sessions, based on previous sleep depth estimates during the previous sleep sessions; and/or based on corresponding volume thresholds for a demographically similar population.

3. The system of claim 1, wherein the one or more hardware processors are further configured to determine sleep depth over time for the first sleep session, the sleep depth over time determination based on (i) the ratio of power in the high frequency band of the EEG signal to power in the low frequency band, (ii) the density of slow waves in the subject, or (iii) the hypnogram for the first sleep session, and wherein the deepening time is an amount of time between two predetermined sleep depth thresholds.

4. The system of claim 1, wherein the one or more hardware processors are configured such that the deepening time is determined by fitting an exponential function to a distribution of contiguous N3 sleep segments in the first sleep session of the subject.

5. The system of claim 1, wherein the one or more hardware processors are configured such that controlling the one or more sensory stimulators to adjust the volume of auditory stimulation provided to the subject during the subsequent sleep session based on the determined rate of volume increase and the output signals during the subsequent sleep session includes:
    determining sleep depth in the subject during the subsequent sleep session based on one or more of the ratio, the density of slow waves, or a peak to peak slow wave amplitude during the subsequent sleep session; and
    controlling the one or more sensory stimulators to adjust the volume of auditory stimulation provided to the subject during the subsequent sleep session based on the determined sleep depth during the subsequent sleep session and the determined rate of volume increase.

6. The system of claim 1, wherein the one or more sensory stimulators comprise a tone generator and/or a speaker.

7. The system of claim 1, wherein the one or more sensors comprise EEG electrodes.

8. A method for adjusting a volume of auditory stimulation delivered to a subject during sleep with an adjustment system, the system comprising one or more sensory stimulators, one or more sensors, and one or more hardware processors, the method comprising:
    providing, with the one or more sensory stimulators, the auditory stimulation to the subject;
    generating, with the one or more sensors, output signals conveying information related to brain activity in the subject;
    determining, with the one or more processors, brain activity parameters in the subject for a first sleep session based on the output signals, the brain activity parameters including a deepening time indicative of a rate at which sleep of the subject deepens during the first sleep session, wherein the deepening time is determined based on (i) a ratio of power in a high frequency band of an electroencephalogram (EEG) signal to power in a low frequency band, (ii) a density of slow waves in the subject, or (iii) a hypnogram for the first sleep session, indicative of sleep depth in the subject during the first sleep session;
    determining, with the one or more processors, a rate of volume increase for auditory stimulation provided to the subject during a subsequent sleep session based on the deepening time; and
    controlling, with the one or more processors, the one or more sensory stimulators to adjust the volume of auditory stimulation provided to the subject during the subsequent sleep session based on the determined rate of volume increase and the output signals during the subsequent sleep session.

9. The method of claim 8, wherein the rate of volume increase is further determined based on a minimum threshold volume and a maximum threshold volume selected for the subject, the minimum threshold volume and the maximum threshold volume selected based on information related to brain activity in the subject from previous sleep sessions, based on previous sleep depth estimates during the previous sleep sessions; and/or based on corresponding volume thresholds for a demographically similar population.

10. The method of claim 8, further comprising determining sleep depth over time for the first sleep session, the sleep depth over time determination based on (i) the ratio of power in the high frequency band of the EEG signal to power in the low frequency band, (ii) the density of slow waves in the subject, or (iii) the hypnogram for the first sleep session, and wherein the deepening time is an amount of time between two predetermined sleep depth thresholds.

11. The method of claim 8, wherein the deepening time is determined by fitting an exponential function to a distribution of contiguous N3 sleep segments in the first sleep session of the subject.

12. The method of claim 8, wherein controlling the one or more sensory stimulators to adjust the volume of auditory stimulation provided to the subject during the subsequent sleep session based on the determined rate of volume increase and the output signals during the subsequent sleep session includes:
    determining sleep depth in the subject during the subsequent sleep session based on one or more of the ratio, the density of slow waves, or a peak to peak slow wave amplitude during the subsequent sleep session; and
    controlling the one or more sensory stimulators to adjust the volume of auditory stimulation provided to the subject during the subsequent sleep session based on the determined sleep depth during the subsequent sleep session and the determined rate of volume increase.

13. The method of claim 8, wherein the one or more sensory stimulators comprise a tone generator and/or a speaker.

14. The method of claim 8, wherein the one or more sensors comprise EEG electrodes.

15. A system for adjusting a volume of auditory stimulation delivered to a subject during sleep, the system comprising:
   means for providing the auditory stimulation to the subject;
   means for generating output signals conveying information related to brain activity in the subject;
   means for determining brain activity parameters in the subject for a first sleep session based on the output signals, the brain activity parameters including a deepening time indicative of a rate at which sleep of the subject deepens during the first sleep session, wherein the deepening time is determined based on (i) a ratio of power in a high frequency band of an electroencephalogram (EEG) signal to power in a low frequency band, (ii) a density of slow waves in the subject, or (iii) a hypnogram for the first sleep session, indicative of sleep depth in the subject during the first sleep session;
   means for determining a rate of volume increase for auditory stimulation provided to the subject during a subsequent sleep session based on the deepening time; and
   means for controlling the means for providing auditory stimulation to adjust the volume of auditory stimulation provided to the subject during the subsequent sleep session based on the determined rate of volume increase and the output signals during the subsequent sleep session.

16. The system of claim 15, wherein the rate of volume increase is further determined based on a minimum threshold volume and a maximum threshold volume selected for the subject, the minimum threshold volume and the maximum threshold volume selected based on information related to brain activity in the subject from previous sleep sessions, based on previous sleep depth estimates during the previous sleep sessions; and/or based on corresponding volume thresholds for a demographically similar population.

17. The system of claim 15, further comprising means for determining sleep depth over time for the first sleep session, the sleep depth over time determination based on (i) the ratio of power in the high frequency band of the EEG signal to power in the low frequency band, (ii) the density of slow waves in the subject, or (iii) the hypnogram for the first sleep session, and wherein the deepening time is an amount of time between two predetermined sleep depth thresholds.

18. The system of claim 15, wherein the deepening time is determined by fitting an exponential function to a distribution of contiguous N3 sleep segments in the first sleep session of the subject.

19. The system of claim 15, wherein controlling the means for providing auditory stimulation to adjust the volume of auditory stimulation provided to the subject during the subsequent sleep session based on the determined rate of volume increase and the output signals during the subsequent sleep session includes:
   determining sleep depth in the subject during the subsequent sleep session based on one or more of the ratio, the density of slow waves, or a peak to peak slow wave amplitude during the subsequent sleep session; and
   controlling the means for providing auditory stimulation to adjust the volume of auditory stimulation provided to the subject during the subsequent sleep session based on the determined sleep depth during the subsequent sleep session and the determined rate of volume increase.

20. The system of claim 15, wherein the means for providing auditory stimulation comprise a tone generator and/or a speaker.

21. The system of claim 15, wherein the means for generating output signals comprise EEG electrodes.

* * * * *